United States Patent [19]

Feller

[11] 4,051,722
[45] Oct. 4, 1977

[54] METHOD AND APPARATUS FOR MEASURING IRREGULARITIES IN THE CROSS-SECTION OF YARNS, ROVING, BANDS AND THE LIKE

[75] Inventor: Peter Feller, Benglen, Switzerland

[73] Assignee: Zellweger Ltd., Uster, Switzerland

[21] Appl. No.: 771,034

[22] Filed: Feb. 22, 1977

[30] Foreign Application Priority Data

Mar. 22, 1976 Switzerland .................. 3559/76

[51] Int. Cl.$^2$ .............................. G01N 33/36
[52] U.S. Cl. ...................... 73/160; 364/470; 364/563; 364/552
[58] Field of Search .............. 73/37.7, 160; 235/151.11, 151.3, 151.32; 250/271, 272

[56] References Cited

U.S. PATENT DOCUMENTS 2,671,199  3/1954  Truit ........................ 73/160
3,303,698  2/1967  Loepfe ..................... 73/160
4,007,457  2/1977  Aeppli ..................... 73/160

Primary Examiner—S. Clement Swisher
Attorney, Agent, or Firm—Werner W. Kleeman

[57] ABSTRACT

A method of, and apparatus for, measuring irregularities in the cross-section of yarns, rovings, bands and the like, by means of a preferably portable measuring apparatus or device providing a direct read-out or display and containing a measuring element, amplifying- and signal converting circuitry as well as an indicator or display device. A measuring signal derived from a yarn irregularity signal is checked with respect to the number of times it passes through at least one given reference value or hysteresis range, and the indicated value for the irregularity constitutes a statistically certain or significant value whenever the number of passes through the reference value or hysteresis range has reached at least a predetermined value.

23 Claims, 7 Drawing Figures

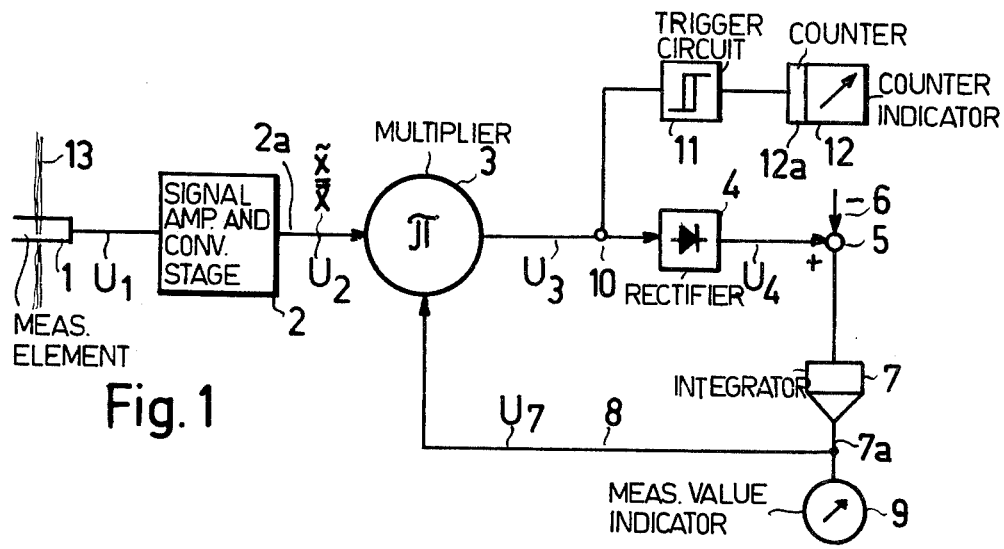
Fig. 1
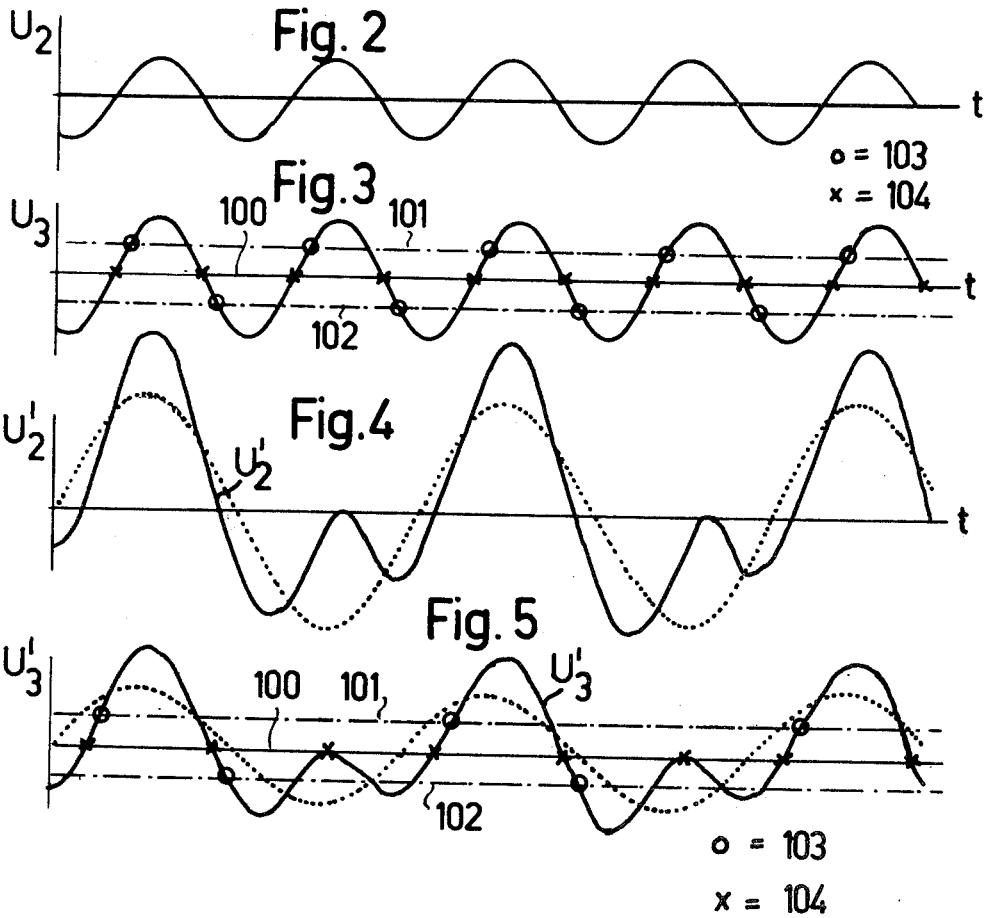
Fig. 2
Fig. 3
Fig. 4
Fig. 5

METHOD AND APPARATUS FOR MEASURING IRREGULARITIES IN THE CROSS-SECTION OF YARNS, ROVING, BANDS AND THE LIKE

BACKGROUND OF THE INVENTION

The present invention relates to a new and improved method of, and apparatus for, measuring the irregularities in the cross-section of yarns, rovings, bands and the like, i.e. a textile structure, and broadly referred to herein simply as a yarn.

Stationary devices for measuring the irregularities in the cross-section of a yarn or the like are quite well known in the textile measuring art. Their measuring principle is predicated upon optical, capacitive, mechanical or other physical devices, by means of which there can be obtained an electrical signal corresponding to the cross-section of the tested material and after having been adequately converted and amplified can be used for indication or display purposes. Such devices are extremely complex in construction since they require a considerable expenditure in equipment in order to obtain a satisfactory measurement consistency, and therefore, they are only suitable for use as a central unit in laboratories, requiring the tested material to be delivered in the form of random samples from the production line. Based upon statistical calculations of the results of the random samples there then must be determined the value of the irregularities which can be used for the entire production.

Furthermore, it is known that the statistical acceptability of a measurement value is dependent upon the length of the evaluated tested material. A further influence is the spectral composition of the irregularities, and specifically, in the sense that the statistical reliability is greater in the case of predominantly short-wave fluctuations than for predominantly long fluctuations. In order to obtain a desired statistical reliability of the measurement result there is thus required a different measuring time, depending upon the speed of the material and the spectral distribution of the irregularities. In the case of laboratory measurements where the speed of movement of the tested material is known, it is possible to determine from tables appropriate minimum measuring times.

Yet, it has been found however, that for continuous checking- and monitoring purposes there must be used a more flexible measuring device which can be employed directly at the production site, at that location placed into operable association with the tested material and after a relatively short period of time can deliver an evaluation value concerning the irregularities.

Textile workers and other people involved in practical production applications with textile materials desire an easy-to-handle, as portable as possible device which can be directly employed at the production site, which after only a brief period of time can deliver a value regarding the momentary irregularity of the tested material and possesses adequate accuracy.

Since the production locations for the tested material, which come under consideration, initially furnish the material at an unknown speed, it was necessary to deviate from the prior practice of adjusting the tested material to a predetermined time interval.

SUMMARY OF THE INVENTION

With the foregoing in mind, it is a primary object of the present invention to provide an improved method of, and apparatus for, measuring irregularities in the cross-section of yarns, rovings, bands and the like, in a manner not associated with the aforementioned drawbacks and limitations of the prior art proposals.

Still another significant object of the present invention aims at the provision of a new and improved method of, and apparatus for, reliably and simply measuring irregularities in the cross-section of textile materials, especially yarns, rovings, bands and the like, while providing measuring apparatus which is extremely easy and simple to use and can be employed conveniently at a desired measuring location due to the portable nature of the equipment.

Now in order to implement these and still further objects of the invention which will become more readily apparent as the description proceeds, the method for measuring the irregularities in the cross-section of yarns, rovings, band and the like, by means of a directly indicating, preferably portable measuring device, containing a measuring element, amplifying- and signal converting circuitry and an indicator or display device, is manifested by the features that a measuring signal, derived from a yarn irregularity signal, is checked with respect to the number of times it passes at least one predetermined reference value or hysteresis range, and the indicated value for the irregularities is then considered as statistically accurate or certain when the number of times it passes through the reference value or hysteresis range reaches at least a predetermined value.

Not only is the invention concerned with the aforementioned method aspects, but as already alluded to above, relates to apparatus for the performance thereof by means of a measuring apparatus or device, which is preferably portable and provides a direct display or indication. This apparatus contains a measuring element, amplifying- and signal converting circuits, as well as a display or indicator device. Further, it contains at least one counter which is connected in circuit with a conductor carrying the measuring signal derived from the yarn irregularity signal, in order to count the passage of the measuring signal through at least one predetermined reference value or hysteresis range. Further, such apparatus contains at least one display or indicator means which, upon reaching a predetermined number of passes through the reference value or hysteresis range, triggers at least one further signal.

According to a special constructional manifestation of the invention, the further signal is employed such that at the display or indicator field for the digital readout of the irregularity value, there is provided an additional field or zone in which there appears a character which indicates to the operator the point in time when the reading of the irregularity value has attained the desired statistical certainty or level of significance.

The dependency of the required measuring time upon the number of passes of the measuring signal through a reference value enables obtaining a result having sufficient accuracy that much quicker the shorter the wave length of the irregularity. Thus, as a function of the material of the tested substance or article and the spectral distribution of the irregularities, the measurement is carried out always only during the minimum required time, something which is particularly advantageous in the case of a portable unit.

As the reference value for the counting of the passage of the measuring signal there can be selected a random or arbitrary threshold value. There is advantageously chosen for this purpose, however, the null potential of the electrical circuit. Further, it is beneficial to provide a reference- or threshold value switch or trigger exhibiting hysteresis which preferably is proportional to the measured irregularites. In this way there is achieved the result that when carrying out measurement at test material having a large proportion of long wave fluctuations the number of passes through the reference value is decreased i.e., the measurement certainty is additionally increased.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 schematically illustrates a principle circuit diagram of a measuring apparatus or device constructed according to the invention;

FIG. 2 is a diagram of a first measuring signal;

FIG. 3 is a diagram of the standardized measuring signal of FIG. 2;

FIG. 4 is a diagram of a further measuring signal;

FIG. 5 is a diagram of the standardized further measuring signal;

DETAILED DESCRIPTION OF THE PREFERRED EMBODIMENTS

Figure 6:
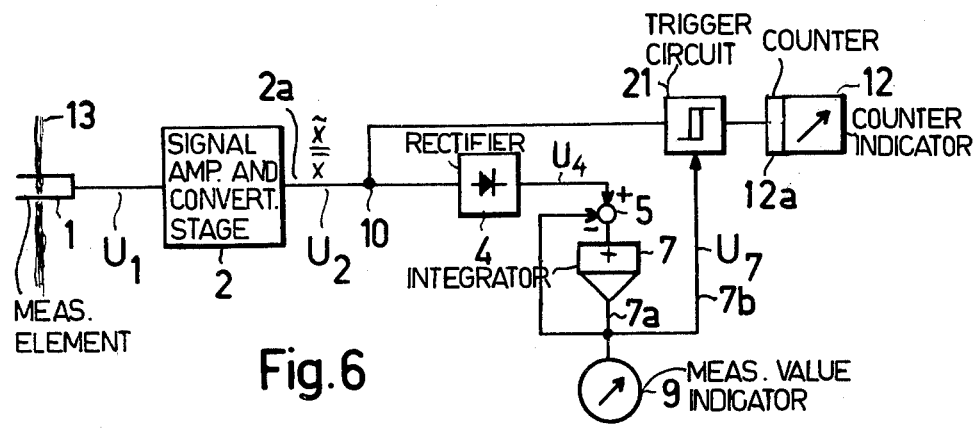
FIG. 6 illustrates a possible modified version of circuitry of the measuring apparatus or device shown in FIG. 1.

Describing now the drawings, FIG. 1 illustrates the principle of a circuit diagram of measuring apparatus or device constructed according to the present invention wherein reference character 1 designates the measuring element which delivers an electrical signal $U_1$ corresponding to irregularities in the cross-section of the throughpassing tested material 13, i.e. typically textile material and hereinafter conveniently broadly termed "yarn." This signal $U_1$ is applied to a signal amplifying- and converting stage 2 at the output 2a of which appears the output signal magnitude $U_2$ which provides a measuring signal $\tilde{x}/\bar{x}$. The symbol $\tilde{x}$ constitutes the momentary deviation of the mean or average value and the symbol $\bar{x}$ the means or average value of the signal $U_1$. This measuring of measurement signal $U_2$ is delivered to a first multiplier 3 where it is multiplied by a factor $U_7$ appearing at the output 7a of an integrator 7. The signal $U_2$ delivered to the multiplier 3 can be amplified or attenuated thereat. The output signal $U_3$ of the multiplier 3 is first of all delivered to a rectifier 4. The direct-current voltage $U_4$ which is formed at the rectifier 4 is correlated at a node or junction point 5 with a reference value 6 and then further processed in integrator 7. The integrator 7 delivers the integrator signal $U_7$ which — as already explained — serves as an input magnitude for the multiplier 3 and also as an indicator or display magnitude which can be read-out at the measuring value-indicator or display 9.

The output voltage $U_3$ is additionally applied from the branch or junction point 10 to a conventional trigger circuit 11 exhibiting hysteresis or backlash properties, and designed such that there is counted the passes of the standardized measuring signal $U_3$ through a reference value. The character of the standardized measuring signal $U_3$, when checking the cross-sectional irregularity of yarns, rovings, bands or the like, in other words textile material, is such that the reference value in the trigger circuit 11 should be different for ascending and descending measurement values, i.e. there should be present a hysteresis of predetermined band width. This can be accomplished by using for instance a Schmitt trigger. This also will be explained more fully hereinafter in conjunction with the description of FIGS. 2 to 5.

The trigger circuit 11 acts upon a counter stage 12a which, after reaching at least a predetermined number of counting steps, controls a counter value-indicator or display 12. The counting of the counter steps is selected such that upon activation of the counter value display 12 the statistical certainty or accuracy of the measurement value appearing at the measurement value-display or indicator 9 falls within a predetermined tolerance.

A preferred embodiment of the counter value display or indicator 12 is constructed such that a first counter value display or read-out occurs when, for instance, there have been accomplished 128 counting steps, and a second counter value display or read-out, which differs from the first, then appears when there have been accomplished a further 384 counter steps, i.e. a total of 512 counter steps, that is to say, four times the number of counter steps have been recorded. If in the first instance, the uncertainty of the measurement value display still amounts to, for instance, 8%, then in the second instance, it will be reduced to 4% since now there has participated approximately four times the amount of tested material in forming the display or indicator value. Any further checking will hardly additionally reduce the uncertainty, since the disturbing influences upon the measurement results do not permit of any greater accuracy. This is however also not contemplated, since the inventive apparatus is not intended to be utilized as a precision instrument, rather as a checking- and monitoring device, where such degree of reliability of the read-out or indication is adequate.

Continuing, in FIG. 2 there is illustrated an approximately sinusoidal measuring signal $U_2$ as a function of time, as the same appears at the output of the signal amplifying- and converting stage 2.

After multiplication with an appropriate factor, corresponding to the irregularity $U_7$ (integrator value) formed in the integrator 7, there is obtained the standardized measuring signal $U_3$. This standardization of the measuring signal serves the purpose of transforming measuring signals having different irregularities to an average or mean amplitude, so that the hysteresis of the triggering stage 11, for counting the throughpasses of the measuring signal $U_3$ i.e. The potential value of the reference values 101 and 102, can be maintained constant. These throughpasses have been indicated in FIG. 3 by the circles 103. In the case of an approximately sinusoidal standardized measuring signal $U_3$ as here indicated, the use of a trigger circuit 11 exhibiting hysteresis or backlash is not absolutely required. The number of fluctuations of the momentary value also could be determined on the basis of the passage of the measuring signal through a fixed reference value 100, which, for instance, may be constituted by the null potential of the circuit. This has been indicated in FIG. 3 by the crosses 104 and leads to the same number. Thus, where applicable, the expression "predetermined reference value", as employed throughout this disclosure and the claims, is used in its broader sense to embrace the different possibilities just mentioned.

The test material 13, consisting of textile material, delivers a signal which is considerably more complicated than the purely sinusoidal shaped signal and for instance has been illustrated by way of example in FIG. 4 by the signal course $U'_2$. It is composed of a short wave and a long wave component which is also the case for the standardized measuring signal $U'_3$ (FIG. 5).

If such measuring signal $U'_3$ is applied to a trigger circuit which does not exhibit hysteresis, then each throughpass of the momentary value of the measuring signal $U'_3$ produces a counting step 104. These accumulate at the sections where the short wave components appear at the region of the reference value 100, so that the predetermined number of throughpassages is reached much too early as long as there is not yet present any statistical certainty or level of significance.

Now if the trigger circuit 11 exhibits hysteresis (reference values 101 and 102), then the throughpasses of the short wave fluctuations through the upper or lower reference value is limited to those instances where the long wave fluctuations likewise extend in an ascending or descending direction. As a consequence thereof, the occurrence of the counting steps 103 is more seldom. This is however intended, since this means that the indication or display regarding obtaining a predetermined reliability of the measurement result which, as mentioned, is dependent upon a predetermined number of counting steps, first occurs after throughpassage of a considerably longer section of the test material, as such is necessary for a signal having predominantly long fluctuations.

Both the course of the measuring signal $U_2$ and $U_3$ respectively, as well as also that of the measuring signal $U'_2$ and $U'_3$ respectively, have been markedly shown in an idealized representation. The fluctuations of the cross-section of spun textile material which arise in reality are even more complicated i.e. consist of fluctuations composed of different wave lengths. Consequently, the advantages from the standpoint of the measuring technology, which can be realized by virtue of the hysteresis of the trigger circuit 11, are still further underscored.

A variation of the circuit arrangement of FIG. 1 has been illustrated in FIG. 6, wherein the same reference characters have been generally used for the same or analogous components. There is dispensed with the formation of a standardized measuring signal $U_3$, but instead there are controlled the reference values for the determination of the hysteresis width or range. From the standpoint of circuit design considerations this is realized inasmuch as the trigger circuit 21 (e.g. Schmitt trigger) possessing the controllable hysteresis or backlash is connected in circuit at the branch or junction point 10 which is located directly at the output 2a of the signal amplifying and converting stage 2. The rectified measuring signal $U_4$ is applied to the integrator 7. The output signal $U_7$ at the integrator output 7a firstly, serves for the display or read-out at the measurement value-indicator or display 9, secondly, as the feedback for the comparison with the measuring signal $U_4$ at the node point or junction 5 and, thirdly, is fed by the control line 7b as the control magnitude for the control or accommodation of the hysteresis range or width at the trigger circuit 21 to the measured irregularity. In the case of smaller irregularities the reference values 101, 102 are applied closer to the base reference value 100, with increasing irregularities they tend to recede therefrom. Also, in consequence thereof there is achieved the beneficial result that with larger irregularities of the tested material 13 the number of passes 103 of the measuring signal through the reference values 101, 102 does not increase over-proportionally, and thus, there is not delivered a measuring value for the irregularity already at a point in time where this measuring value has not yet been sufficiently statistically secured or made certain.

Figure 7:
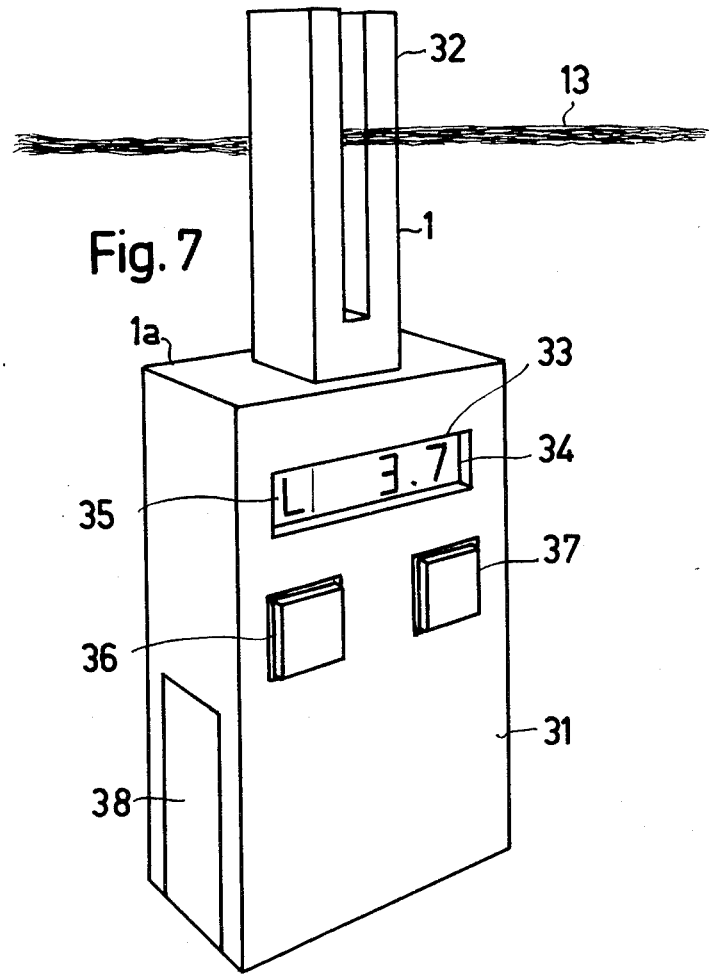
FIG. 7 is a perspective view of an embodiment of measuring apparatus or device according to the present invention.

A preferred exemplary embodiment of the inventive apparatus has been shown in perspective view of FIG. 7. Arranged in a housing 31 is a battery-powered electrical circuit of the type previously discussed above, so that the apparatus or device can be used independent of the power supply network. At the end 1a of the device there is provided a measuring element 1, for instance a measuring capacitor 32, or, however, a plug device for receiving a cable for connecting the evaluation circuit with a measuring capacitor. The housing surface contains a display or read-out window 33 behind which there is visible the indicator or display means 34 for the measured irregularity value as well as a further indicator or display means 35 for the reading of the predetermined number of counting steps which have occurred. As the read-out or indicator means there is advantageously used a digital display having luminescent characters which, with small energy consumption, provides a clear and readily discernible numerical display. The characters used for the reading of the textile material-irregularity can be designed as numbers, letters, or as other symbols.

Additionally, there are accommocated at the housing 31 a null position key 36 and a measuring key 37, by means of the latter of which there can be initiated the measurement operation in that at the start of measurement, by depressing the first key 36 there is extinguished the prior display value, and upon depressing the second key 37 there is initiated the integration operation. The display means also can be additionally constructed such that testing of the condition of the battery charge is possible. Behind a detachable cover 38 in the housing 31 there are arranged, for instance, the batteries so as to be easily exchangeable. It is, however, also possible to use as the current supply rechargeable accumulators.

While there are shown and described present preferred embodiments of the invention, it is to be distinctly understood that the invention is not limited thereto, but may be otherwise variously embodied and practiced within the scope of the following claims.

Accordingly, what I claim is:

1. A method of measuring irregularities in the cross-section of textile materials, especially yarns, rovings, bands and the like, comprising the steps of:

testing the textile material for detecting irregularities in its cross-section;

deriving a textile material-irregularity signal from the detected irregularities;

deriving a measuring signal from the textile material-irregularity signal;

checking the measuring signal with respect to the number of times it passes through at least one predetermined reference value or a hysteresis range to thereby form an indicator value; and classifying the indicator value for the irregularities as statistically of significance when the number of passes through the reference value or hysteresis range has reached at least a predetermined value.

2. The method as defined in claim 1, including the step of:
adjusting the spacing of the reference values or the hysteresis range substantially proportional to the magnitude of the derived measuring signal.

3. The method as defined in claim 1, further including the steps of:
calculating from the number of passes of the derived measuring signal a magnitude for judging the statistical reliability of the measurement result; and indicating such magnitude.

4. The method as defined in claim 1, further including the steps of:
standardizing the measuring signal derived from the textile material-irregularity signal with respect to its amplitude to a substantially constant irregularity value.

5. The method as defined in claim 4, further including the steps of:
applying a signal representative of the measured irregularity to a multiplier where the textile material-irregularity signal obtained from a signal amplifying and converting circuit is processed in accordance with the existing irregularity.

6. The method as defined in claim 5, wherein:
processing of the signal is accomplished by amplification thereof.

7. The method as defined in claim 5, wherein:
processing of the signal is accomplished by attenuation thereof.

8. The method as defined in claim 5, further including the step of:
characterizing the attainment of a statistically significant textile material-irregularity value by the appearance of a character in a read-out window of an indicator means.

9. The method as defined in claim 8, further including the steps of:
utilizing at the indicator means a first character for a lower degree of statistical significance of the textile material irregularity and at least one further character for at least an increased degree of statistical significance.

10. The method as defined in claim 1, further including the steps of:
rectifying the textile material-measuring signal and forming a mean value therefrom; and
employing the thus formed signal as an indicator- and control signal for controlling the band width of the predetermined reference values of the hysteresis range of a trigger circuit.

11. The method as defined in claim 1, further including the step of:
utilizing as a reference potential for the reference values the null potential of a circuit used for measurement of the irregularities of the textile material.

12. A method of measuring irregularities in the cross-section of textile materials, especially yarns, rovings, bands and the like, comprising the steps of:
examining the textile material for detecting irregularities in its cross-section;
deriving a textile material-irregularity signal from the detected irregularities; deriving a measuring signal from the textile material-irregularity signal;
checking the measuring signal with respect to the number of times it passes through at least one predetermined reference value to thereby form an indicator value; and
classifying the indicator value for the irregularities as statistically of significance when the number of passes through the reference value has reached at least a predetermined value.

13. An apparatus for measuring the irregularities in the cross-section of textile materials, especially yarns, rovings, bands and the like, comprising:
a measuring element for producing a textile material-irregularity signal from the textile material;
amplifying- and signal converting circuit means operatively connected with said measuring element for producing a textile material-measuring signal from said textile material-irregularity signal;
an indicator device for displaying the measured irregularities in the cross-section of the textile material;
said circuit means containing a conductor carrying the textile material-measuring signal derived from the textile material-irregularity signal;
a counter connected with said conductor for counting the passage of the textile material-measuring signal through at least one predetermined reference value; and
at least one indicator means which, upon reaching a predetermined number of passes of the textile material-measuring signal through said at least one predetermined reference value, delivers at least one further signal.

14. The apparatus as defined in claim 13, wherein:
said at least one predetermined reference value comprises a hysteresis range and said counter counts the passage of the textile material-measuring signal through said hysteresis range.

15. The apparatus as defined in claim 14, further including:
a trigger circuit exhibiting hysteresis connected forwardly of and in circuit with said counter.

16. The apparatus as defined in claim 15, wherein:
the hysteresis of said trigger circuit is governed by the potential difference between two reference values which can be controlled substantially proportional to the textile material-irregularity signal.

17. The apparatus as defined in claim 15, wherein:
the hysteresis of said trigger circuit is defined by a potential difference prevailing between two reference values.

18. The apparatus as defined in claim 15, further including:
means for standardizing the textile material-measuring signal with respect to its amplitude which is applied to the trigger circuit exhibiting hysteresis, by means of the measured textile material-irregularity signal.

19. The apparatus as defined in claim 17, further including:
means for controlling the potential difference between said reference values by the measured textile material-irregularity signal.

20. The apparatus as defined in claim 13, wherein:
the signal delivered by the indicator means constitutes an indication that the indicated value of the measured irregularities in the cross-section of the textile material possesses a predetermined degree of statistical significance.

21. The apparatus as defined in claim 20, wherein:
said indicator means delivers a number of signals associated with an increasing number of counting steps in the counter, to thereby detect different stages of the statistical significance of the indicated value for the measured irregularities in the cross-section of the textile material.

22. The apparatus as defined in claim 21, wherein:
said indicator means includes a read-out window;
the different stages of statistical significance appear as a visible read-out in the form of different characters associated with said different stages of statistical significance.

23. An apparatus for measuring the irregularities in the cross-section of textile materials, especially yarns, rovings, bands and the like, comprising:
a measuring element for producing a textile material-irregularity signal from the textile material;
amplifying- and signal converting circuit means operatively connected with said measuring element for producing a textile material-measuring signal from said textile material-irregularity signal;
an indicator device for displaying the measured irregularities in the cross-section of the textile material;
a counter connected with said circuit means for counting the passage of the textile material-measuring signal through at least one predetermined reference value; and
at least one indicator means which, upon reaching a predetermined number of passes of the textile material-measuring signal through said at least one predetermined reference value, provides an indication of the statistical significance of the measured irregularities in the cross-section of the textile material displayed by the indicator device.

* * * * *